(12) United States Patent
Doerr (10) Patent No.: US 8,244,353 B2
(45) Date of Patent: Aug. 14, 2012

(54) ANTITACHYCARDIAC HEART STIMULATOR

(75) Inventor: Thomas Doerr, Berlin (DE)

(73) Assignee: Biotronik CRM Patent AG (CH)

( * ) Notice: Subject to any disclaimer, the term of this patent is extended or adjusted under 35 U.S.C. 154(b) by 548 days.

(21) Appl. No.: 12/475,629

(22) Filed: Jun. 1, 2009

(65) Prior Publication Data

US 2009/0306731 A1    Dec. 10, 2009

(30) Foreign Application Priority Data

Jun. 9, 2008 (DE) .......................... 10 2008 002 293

(51) Int. Cl.
*A61N 1/362* (2006.01)
(52) U.S. Cl. .............................................. 607/14; 607/5
(58) Field of Classification Search .................. 607/5, 9, 607/14, 25
See application file for complete search history.

(56) References Cited

U.S. PATENT DOCUMENTS

| | | | |
|---|---|---|---|
| 5,591,215 A | 1/1997 | Greenhut et al. | |
| 6,434,424 B1 | 8/2002 | Igel et al. | |
| 6,611,713 B2 * | 8/2003 | Schauerte | 607/14 |
| 2003/0199928 A1 | 10/2003 | Hsu et al. | |
| 2004/0171958 A1 | 9/2004 | Fitts et al. | |
| 2005/0149125 A1 | 7/2005 | Kim et al. | |
| 2006/0217621 A1 | 9/2006 | Kim et al. | |
| 2008/0177340 A1 | 7/2008 | Kim et al. | |

FOREIGN PATENT DOCUMENTS

WO   WO 2004/071576 A   8/2004
WO   WO 2005/065772 A   7/2005

OTHER PUBLICATIONS

European Search Report, EP 09 15 9863, Aug. 14, 2009.

* cited by examiner

*Primary Examiner* — Brian T Gedeon
(74) *Attorney, Agent, or Firm* — Craig A. Fieschko, Esq.; DeWitt Ross & Stevens S.C.

(57) ABSTRACT

An implantable cardiac stimulator includes a cardioversion/defibrillation unit connected to at least one electrode pair for generation and delivery of cardioversion or defibrillation shocks; an atrial sensing unit detecting atrial contraction, and outputting an atrial sensing signal indicating a atrial event when an atrial contraction is detected; a ventricular sensing unit detecting ventricular contraction, and outputting a ventricular sensing signal when a ventricular contraction is detected; a tachycardia detection unit connected to the atrial and ventricular sensing units and detecting a tachycardia, and classifying it as a ventricular tachycardia (VT) or as a supraventricular tachycardia (SVT); and a treatment control unit designed to trigger at least one atrial cardioversion shock when a ventricular rhythm detected by the ventricular sensing unit is faster than a programmed frequency limit, and the tachycardia detection unit classifies an SVT as an atrial fibrillation (AFib).

20 Claims, 7 Drawing Sheets

ANTITACHYCARDIAC HEART STIMULATOR

FIELD OF THE INVENTION

The invention relates to an implantable cardiac stimulator for treatment of tachycardiac arrhythmias. Such a cardiac stimulator is also known as an implantable cardioverter/defibrillator (ICD) and usually also fulfills the function of an implantable cardiac pacemaker.

BACKGROUND OF THE INVENTION

Tachycardiac arrhythmias may be classified as tachycardias in the narrower sense, in which the affected chamber of the heart (ventricle or atrium) contracts in an orderly manner but at a high, physiologically inappropriate rate. In fibrillation, however, there is an unordered contraction of the respective chamber because of a recurring stimulus in which the particular chamber makes practically no further contribution toward pumping a volume of blood.

Tachycardias may also be differentiated according to their site of occurrence. Ventricular tachycardias (VT) originate in the ventricle, whereas supraventricular tachycardias (SVT) originate above the ventricle, e.g., in the atrium.

Implantable cardiac stimulators in the form of cardiac pacemakers or cardioverter/defibrillators are known in the art. Such cardiac simulators are usually connected to electrode lines, which have stimulation electrodes and optionally additional defibrillation electrodes in a chamber of the heart or in the immediate vicinity thereof. A cardiac pacemaker may deliver an electric stimulation pulse to the muscle tissue of a chamber of a heart via a stimulation electrode to thereby induce a stimulated contraction of the chamber of the heart if the stimulation pulse is of a sufficient intensity and the myocardial tissue (myocardium) is not at that moment in a refractory phase. To trigger a stimulated contraction of a heart chamber in this way, electrode lines with relatively small-area stimulation electrodes are usually used because to trigger a stimulated contraction of a heart chamber, it is sufficient if only a small portion of the myocardium of this chamber is initially stimulated. Such a stimulated contraction of a heart chamber is referred to within the context of this description as a "stimulated event." If a natural contraction of the chamber occurs, it is referred within the context of this description as an "intrinsic" or "natural" action or event. A contraction of the right atrium of the heart, for example, is referred to as an atrial event, and may be a natural atrial event, or in the case of an atrial pacemaker, may be a stimulated atrial event. In the same sense, natural (intrinsic) and stimulated left-ventricular and right-ventricular events are differentiated.

Local stimulation of the myocardium propagates by stimulus conduction from the stimulation site in the myocardium and leads to depolarization of the muscle cells, and thus to contraction of the myocardium. After a short period of time, repolarization of the muscle cells occurs and thus a relaxation of the myocardium. During the depolarization phase, myocardial cells are not sensitive to stimulus, i.e., they are refractory. The electric potentials associated with depolarization and repolarization can be detected and their course over time can be analyzed in the form of an electrocardiogram.

Natural (intrinsic) events are detected by deriving the electric potentials of the myocardium of the respective heart chamber with the help of sensing electrodes, which are part of a corresponding electrode line. The sensing electrodes may also at the same time be the stimulation electrodes, and may ultimately be used alternately as stimulation electrodes and as sensing electrodes. An electrode pair, comprising a tip electrode and a ring electrode, is typically provided for this sensing, the tip electrode also serving as a stimulation electrode. A bipolar intracardiac electrocardiogram (IEGM) is obtained in this way. Sensing and stimulation in the ventricle are performed with the help of a ventricular electrode line, and similarly sensing and stimulation in the atrium (in the right atrium) are performed using an atrial electrode line, with the ventricular and atrial lines being connected separately to the respective cardiac stimulator. In addition, a left-ventricular electrode line may also be provided, typically protruding into the vicinity of the left ventricle through the coronary sinus and a lateral vein branching off from the former, and may have a small-area stimulation electrode and/or sensing electrode there.

During operation of the cardiac stimulator, the sensing electrodes are connected to corresponding sensing units, which are designed to analyze a respective electrocardiogram recorded by using a sensing electrode (and/or a pair of sensing electrodes). In particular, the sensing electrodes detect atrial and/or ventricular events, i.e., natural atrial or ventricular contractions. This is done, for example, by comparing threshold values, i.e., an intrinsic event is detected when a particular intracardiac electrocardiogram exceeds a suitable predefined threshold value.

The particular intrinsic atrial heart rate (atrial frequency) and/or ventricular heart rate (ventricular frequency) may be derived from the frequency at which atrial and/or ventricular events follow one another. Tachycardias, for example, can be detected in this way.

The ICDs currently available on the market offer a number of functions for termination of atrial arrhythmias, in particular atrial fibrillation, by cardioversion shocks that are delivered automatically. These cardioversion shocks are triggered repeatedly in response to detection of an atrial fibrillation. Here, the ventricular rhythm is evaluated only for more reliable synchronization of the shock.

All of the currently known devices deliver these cardioversion shocks either independently of the ventricular rhythm, or deliver no cardioversion shock when the ventricular frequency exceeds a programmable value. In many applications, atrial cardioversion is allowed only at certain times of the day or night and may first be delayed to give preference to a spontaneous termination, if necessary.

There is still no sufficiently specific algorithm for treatment of atrial fibrillation to permit adequate treatment of cardiac insufficiency patients with persistent atrial fibrillations. In these patients, atrial fibrillation always requires treatment when the atrial fibrillation is rapidly conducted into the ventricle. These patients lose the ventricular filling component due to an optimized AV time due to the atrial fibrillation. If the ventricular response exceeds a certain frequency, these patients also lose ventricular resynchronization, and with an increase in ventricular frequency, at the same time the cardiac output drops with an increase in myocardial oxygen demand. This leads to rapid decompensation in these patients. Immediate cardioversion of the atrial fibrillation is the only effective therapy here if the risk of thrombosis can be largely ruled out.

SUMMARY OF THE INVENTION

An object of the invention is to create a cardiac stimulator that will terminate atrial tachycardia at a suitable point in time.

According to the invention, an implantable cardiac stimulator is provided for electric antitachycardiac treatment of the heart:

having at least one atrial and one ventricular sensing unit and having at least one shock generator for defibrillation/cardioversion shock therapy, having a discrimination unit designed to differentiate ventricular (VT) and supraventricular tachycardias (SVT) and having a control unit that is connected to the shock generator for triggering an atrial cardioversion shock, the control unit being configured such that at least one atrial cardioversion shock is triggered when the ventricular rhythm is initially faster than a programmed frequency limit and at the same time the discrimination unit classifies an SVT as an atrial fibrillation (AFib).

The control unit is capable of detecting a particular intrinsic atrial and/or ventricular cardiac rhythm with a corresponding atrial frequency and/or ventricular frequency in a known way by means of natural (intrinsic) atrial and/or ventricular events detected by the atrial and ventricular sensing units.

An implantable cardiac stimulator according to the invention thus includes at least a cardioversion/defibrillation unit, which is or can be connected to at least one electrode pair for defibrillation/cardioversion shock therapy and is designed as a shock generator to generate and deliver cardioversion shocks or defibrillation shocks, an atrial sensing unit designed to detect an atrial contraction and, in the case when an atrial contraction is detected, to deliver an atrial sensing signal indicating a respective atrial event, a ventricular sensing unit designed to detect a respective ventricular contraction and in the case when a ventricular contraction is detected, to deliver a ventricular sensing signal, a tachycardia detection unit, which is connected to the atrial and ventricular sensing units and is designed to detect a tachycardia, where the tachycardia detection unit is also designed as a discrimination unit to classify a detected tachycardia as a ventricular tachycardia (VT) or a supraventricular tachycardia (SVT), and a treatment control unit, which is connected to the cardioversion/defibrillation unit for triggering an atrial cardioversion shock and is designed to trigger at least one atrial cardioversion shock when initially a ventricular rhythm detected by the ventricular sensing unit is faster than a programmed frequency limit and at the same the tachycardia detection unit classifies an SVT as an atrial fibrillation (AFib).

An object of the invention is to always terminate an atrial fibrillation immediately in patients with chronic cardiac insufficiency when the resulting ventricular frequency exceeds a limit value. This limit value is individual for each patient and should be adjustable by a physician. In this cardioversion, the risk of a stroke (release of a thrombus in the cardiovascular system) should be minimized if at all possible.

The control unit is preferably designed to trigger atrial cardioversion only when the ventricular rhythm is faster than a programmable frequency limit but slower than the atrial rhythm and the ventricular rhythm is irregular, i.e., does not meet a predefined stability criterion.

Furthermore, in a preferred cardiac stimulator, its treatment control unit is designed to always synchronize an atrial cardioversion with an R wave, i.e., a detected intrinsic event in the ventricle.

The cardioversion/defibrillation unit is or can be connected preferably to at least three shock electrodes, namely a distal shock coil, a proximal shock coil on the right-ventricular electrode line, and an electrically conductive housing of the implantable cardiac stimulator.

In addition, the cardioversion/defibrillation unit is designed in combination with the treatment control unit so that each cardioversion/defibrillation unit is connected to at least two shock electrodes for an atrial cardioversion and for a ventricular defibrillation, at least one shock electrode thereof for atrial cardioversion being different from the shock electrode for ventricular defibrillation, so that a different shock path can be established for atrial cardioversion than for ventricular defibrillation. The cardioversion/defibrillation unit for atrial cardioversion may be connected to the proximal shock coil of the right-ventricular electrode line and to the housing of the implantable cardiac stimulator, for example, and the cardioversion/defibrillation unit for ventricular defibrillation may be connected to the distal shock coil of the right-ventricular electrode line and to the housing of the implantable cardiac stimulator.

In addition, the implantable cardiac stimulator is preferably a biventricular three-chamber cardiac pacemaker, which is and/or can be connected to one atrial electrode line and to two ventricular electrode lines, namely a right-atrial electrode line, a right-ventricular electrode line and a left-ventricular electrode line. Such a cardiac stimulator may be used for cardiac resynchronization therapy (CRT) and has a left-ventricular sensing unit, which is or can be connected to a sensing electrode on the left-ventricular electrode line and is designed to detect intrinsic left-ventricular events.

With such a cardiac stimulator, the treatment control unit is preferably connected to the atrial and to the left-ventricular sensing units.

The treatment control unit is preferably also designed to always synchronize the atrial cardioversion to a detected left-ventricular R wave.

The implantable cardiac stimulator preferably has a timer which is connected to the atrial sensing unit and is designed to monitor whether an atrial fibrillation exceeds a predefined period of time without interruption. If this time is exceeded, the atrial cardioversion is then triggered.

The treatment control unit is preferably programmable, such that the triggering of an automatic atrial cardioversion by a programmable parameter can be turned on and/or off. To do so, the implantable cardiac stimulator is preferably equipped with a telemetry unit and a memory for program parameters, so that the implantable cardiac stimulator is remotely programmable from the outside.

BRIEF DESCRIPTION OF THE DRAWINGS

The present invention will now be explained in greater detail on the basis of an exemplary embodiment with reference to the figures, in which.

DETAILED DESCRIPTION OF PREFERRED VERSIONS OF THE INVENTION

Figure 1:
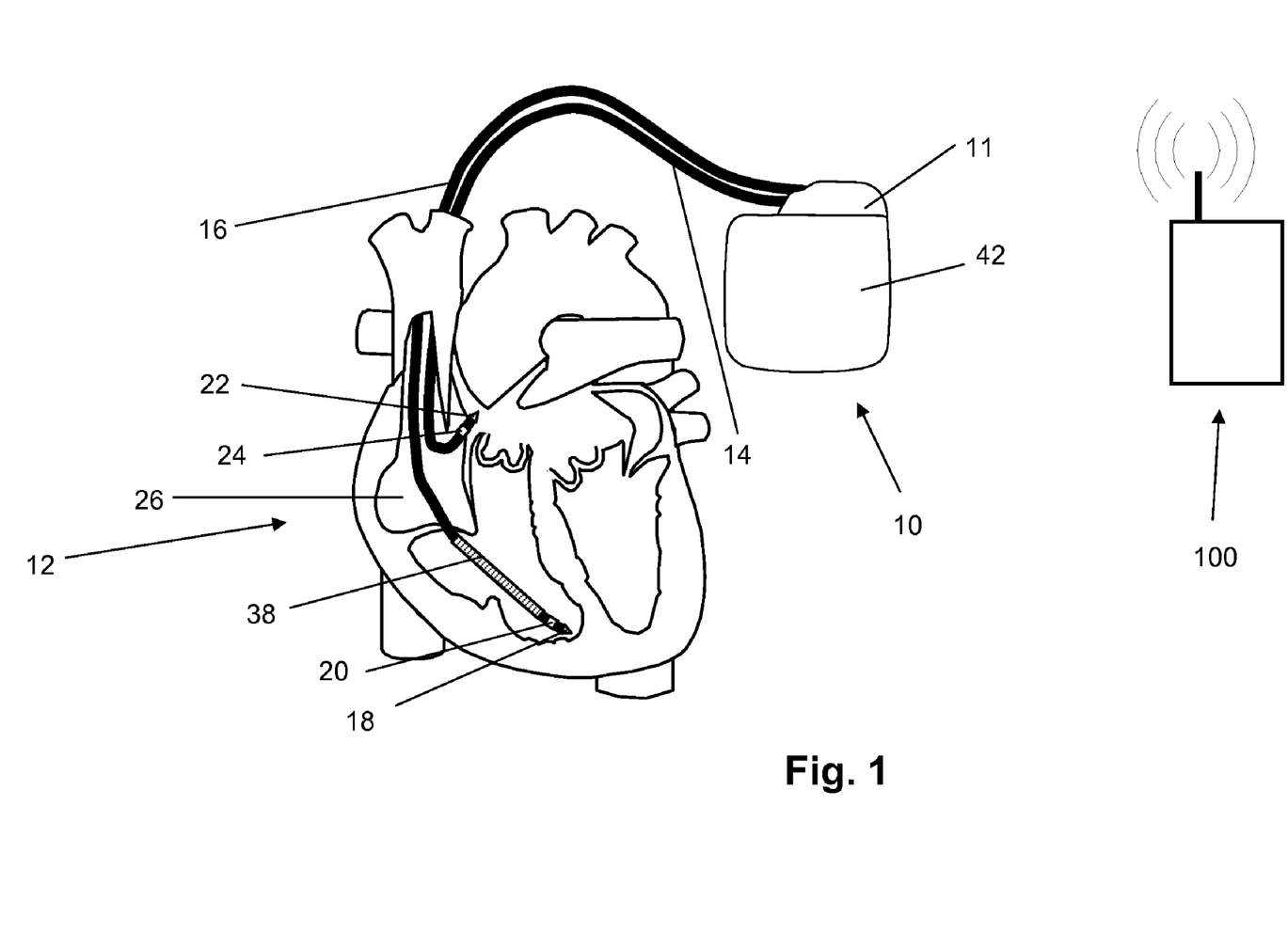
FIG. 1 shows an implantable cardiac stimulator in the form of a two-chamber cardiac pacemaker connected to a patient device.

FIG. 1 shows a two-chamber cardiac pacemaker and implantable cardioverter/defibrillator (ICD) as an implantable cardiac stimulator 10. This two-chamber cardiac pacemaker is connected by electrode lines 14 and 16 to stimulation and sensing electrodes 18 and 20 and/or 22 and 24 in the ventricle and/or the atrium of the heart, respectively, and in this way can deliver stimulation pulses to the heart and can also receive electric potentials from the heart.

Furthermore, an external device 100 near the implantable cardiac stimulator 10 is also shown.

The electrode lines 14 and 16 are electrically connected by known standardized plug connections to sockets in a header (terminal housing) 11 of the cardiac stimulator 10. In this way, the electrode lines 14 and 16 are also connected to electronic components in the interior of a hermetically sealed metal housing 42 of the cardiac stimulator 10. These components are diagramed schematically below and determine the functioning of the cardiac stimulator 10.

The electrode line 14 is a right-atrial electrode line having an atrial tip electrode (RA tip) 22 at its distal end and having an atrial ring electrode (RA ring) 24 at a short distance therefrom, both of these electrodes being placed in the right atrium 26 of the heart 12.

The electrode line 16 is a right-ventricular electrode line having on its distal end a right-ventricular tip (RV tip) 18 and a nearby right-ventricular ring electrode (RV ring) 20. The two electrodes are arranged in the apex of the right ventricle of the heart.

Furthermore, the right-ventricular electrode line 16 also has a right-ventricular shock coil (RV coil) 38 as a large-area electrode for delivering defibrillation shocks.

Figure 2:
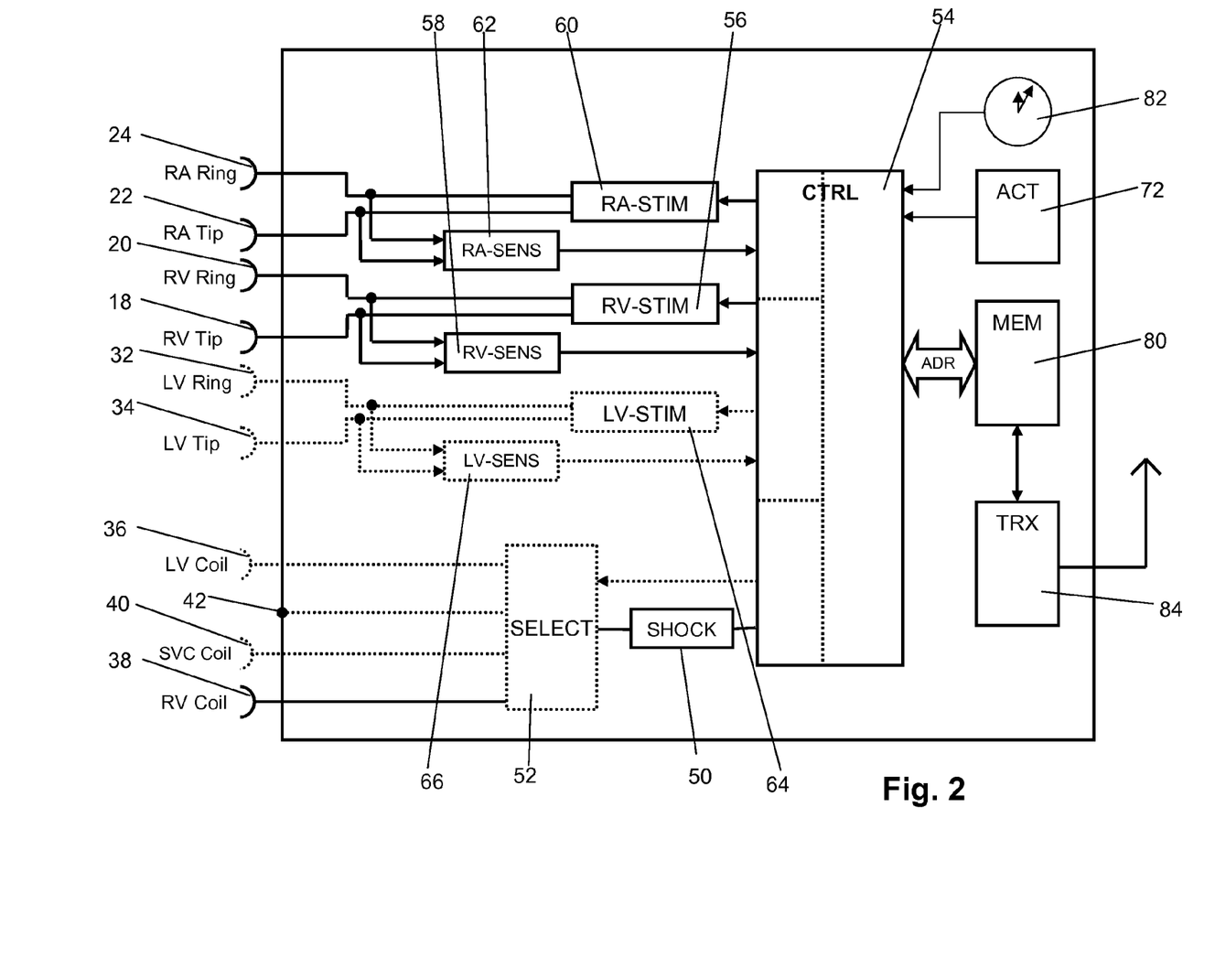
FIG. 2 shows an overview diagram of the implantable cardiac stimulator.

FIG. 2 shows the main components of the cardiac stimulator 10. Furthermore, additional components, such as those which may additionally be provided in an alternative version of the implantable cardiac stimulator 10, are also shown in the dashed-line diagram (see FIG. 5 for further details regarding such an alternative stimulator 10').

The electric terminals for the various electrodes 18, 20, 22, 24 and 38 are shown on the left side. The shock electrode (shock coil) 38 is connected to a shock pulse generator 50. The shock generator 50 is connected to a stimulation control unit 54, which controls the shock pulse generator 50 as needed to generate and deliver a cardioversion shock or a defibrillation shock.

The terminal for the right-ventricular tip electrode (RV tip) 18 and the terminal for the right-ventricular ring electrode (RV ring) 20 are each connected to both a right-ventricular stimulation unit 56 and a right-ventricular sensing unit 58. Both the right-ventricular stimulation unit 56 and the right-ventricular sensing unit 58 are connected to the stimulation control unit 54.

The right-ventricular stimulation unit 56 is designed to generate a right-ventricular stimulation pulse in response to a control signal of the stimulation control unit 54 and to then deliver it to the right-ventricular ring electrode (RV ring) 20 and the right-ventricular tip electrode (RV tip) 18. Alternatively, it is also possible for the housing 42 of the cardiac stimulator 10 to form a neutral electrode and for the right-ventricular stimulation unit 56 to be connected to the terminal for the right-ventricular tip electrode (RV tip) 18 and the housing 42 as another electrode for delivery of a stimulation pulse. A right-ventricular stimulation pulse differs from a defibrillation shock in that the stimulation pulse has a much lower pulse intensity so that it does not stimulate all the myocardial tissue (myocardium) of a heart chamber all at once, like a defibrillation shock, but instead stimulates only the myocardial cells in the immediate vicinity of the right-ventricular tip electrode (RV tip) 18. This stimulation then propagates through natural stimulus conduction over the entire ventricle and thereby ensures a stimulated contraction of the ventricle.

The right-ventricular sensing unit 58 is designed to first amplify and then filter the electric potentials applied to the terminal for the right-ventricular ring electrode (RV ring) 20 and the right-ventricular tip electrode (RV tip) 18 through an input amplifier. In addition, the right-ventricular sensing unit 58 is designed to analyze the course of the electric signals applied at its inputs, such that the right-ventricular sensing unit 58 automatically detects a natural (intrinsic), i.e., automatic contraction of the right ventricle. This may take place, for example, by comparing the characteristic of the signal applied to the inputs of the right-ventricular sensing unit 58 with a threshold value. Typically the largest amplitude of the signal in the form of the so-called R wave is characteristic of a natural contraction of the right ventricle, which can be detected by threshold value comparison. The right-ventricular sensing unit 58 then delivers to the stimulation control unit 54 a corresponding output signal indicating a natural contraction of the right ventricle.

Similarly the terminal for the right-atrial tip electrode (RA tip) 22 and the terminal for the right-atrial ring electrode (RA ring) 24 are each connected to a right-atrial stimulation unit 60 as well as to a right-atrial sensing unit 62, each of which is in turn connected to the stimulation control unit 54. The right-atrial stimulation unit 60 is designed to generate stimulation pulses of an intensity sufficient to stimulate the right-atrial myocardium. The right-atrial stimulation pulses may have a different pulse intensity than the right-ventricular stimulation pulses. The right-atrial sensing unit 62 is designed to detect a so-called P-wave characteristic of a natural (intrinsic) contraction of the right atrium from the characteristic of the differential signal applied at its inputs. If the right-atrial sensing unit 62 detects a corresponding P wave, it generates an output signal and delivers this signal, characterizing an intrinsic right-atrial contraction, to the stimulation control unit 54.

As another component of the cardiac stimulator 10, an activity sensor 72 is connected to the stimulation control unit 54. The activity sensor 72 is designed to detect a signal, e.g., a motion signal, which depends on a patient's physical activity and to deliver a corresponding signal indicating the patient's physical activity to the stimulation control unit 54. This makes it possible for the stimulation control unit 54 to adjust the timing of the simulation pulses to the patient's needs (hemodynamic demand).

In addition, the cardiac stimulator 10 includes a memory unit 80 connected to the stimulation control unit 54, with the memory unit 80 making it possible to store signals generated or analyzed by the stimulation control unit 54. The memory unit 80 also or alternatively makes it possible to store control programs for the stimulation control unit 54 in a rewritable form. The stimulation control unit 54 is also connected to a timer 82.

The cardiac stimulator 10 has at least bidirectional telemetry interface 84 to be able to transmit stored data from the electronic implant to an external device 100 and conversely to also be able to receive programming settings and treatment commands from this external device 100.

Figure 3:
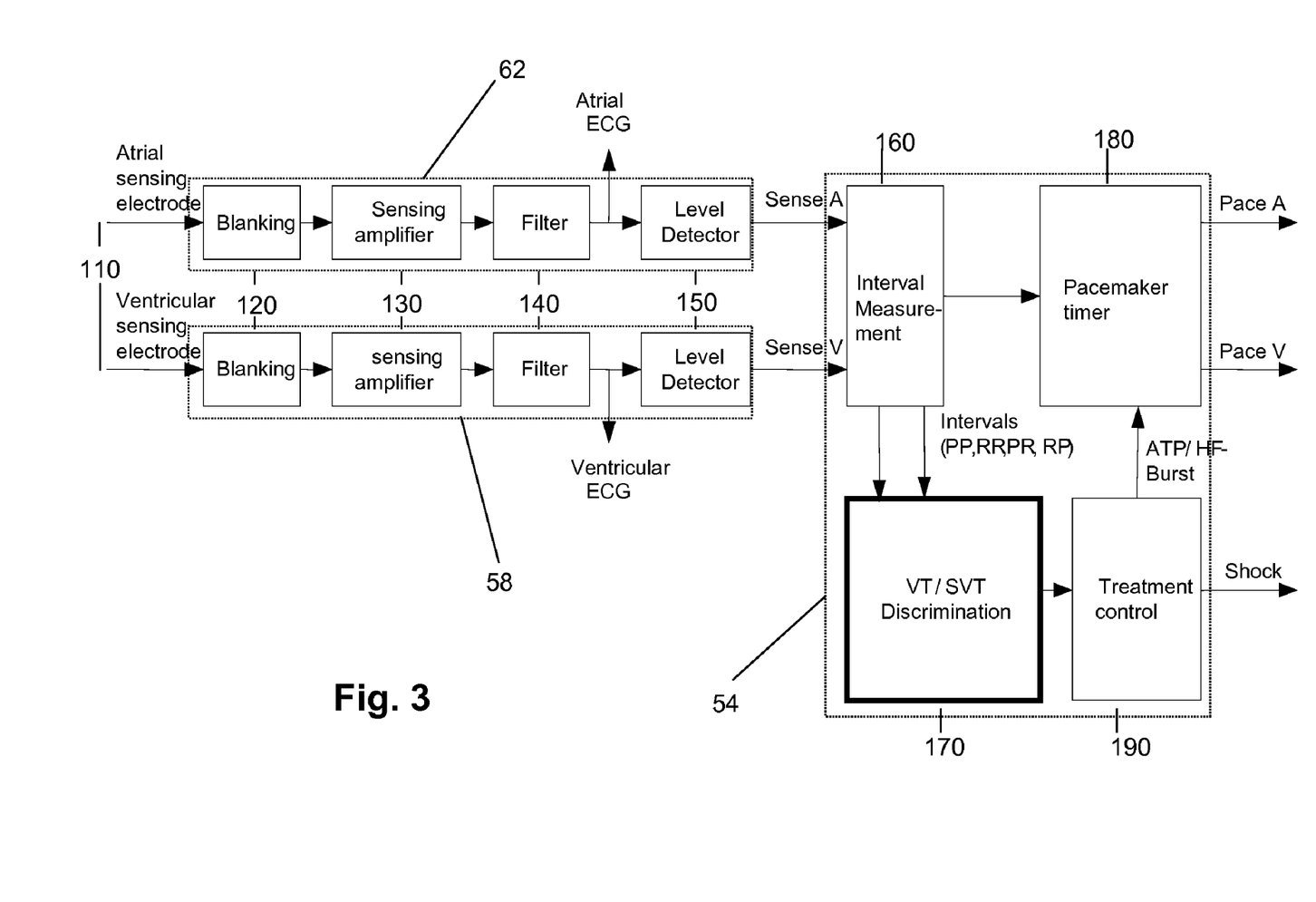
FIG. 3 shows a detailed block diagram of an expanded discrimination unit for atrial cardioversion of the implantable cardiac stimulator.

FIG. 3 shows a detail of a detailed block diagram of a two-chamber ICD, including the expanded discrimination unit 170 for atrial cardioversion.

FIG. 3 shows the atrial sensing unit 62 and the right-ventricular sensing unit 58 (or, if present, the left-ventricular sensing unit 66 of FIG. 2) in a detailed diagram. The intracardiac signals derived by means of atrial and/or ventricular sensing electrodes 110 are first amplified, with a blanking stage 120 being connected upstream from each amplifier 130 to blank out stimulation artifacts. Then the respective signal is digitized and filtered at filter 140 and relayed to a comparator 150 for detection of P waves and/or R waves.

Further signal processing then takes place in control unit 54.

The P waves and R waves of synchronous events detected by the atrial sensing unit 62 and/or the right-ventricular sensing 58 are measured in an interval measuring unit 160. These PP, PR, RP and RR intervals (i.e., the times between consecutive P/R waves) are forwarded to a pacemaker timer 180 for control of the antibradycardiac stimulation. Furthermore, this interval information is compared in the VT/SVT discrimination unit 170 that serves as an interval analyzer for discrimination between VT and SVT with regard to their ratios in terms of the atrial and ventricular rhythm and is made available in evaluated form to the detection and treatment control unit 190 for antitachycardiac treatment (HF burst, ATP, shock).

The VT/SVT discrimination unit 170 is expanded, so that an atrial cardioversion shock is always requested by the treatment control unit 190 when a tachycardiac ventricular rhythm due to an atrial fibrillation is classified.

Figure 4:
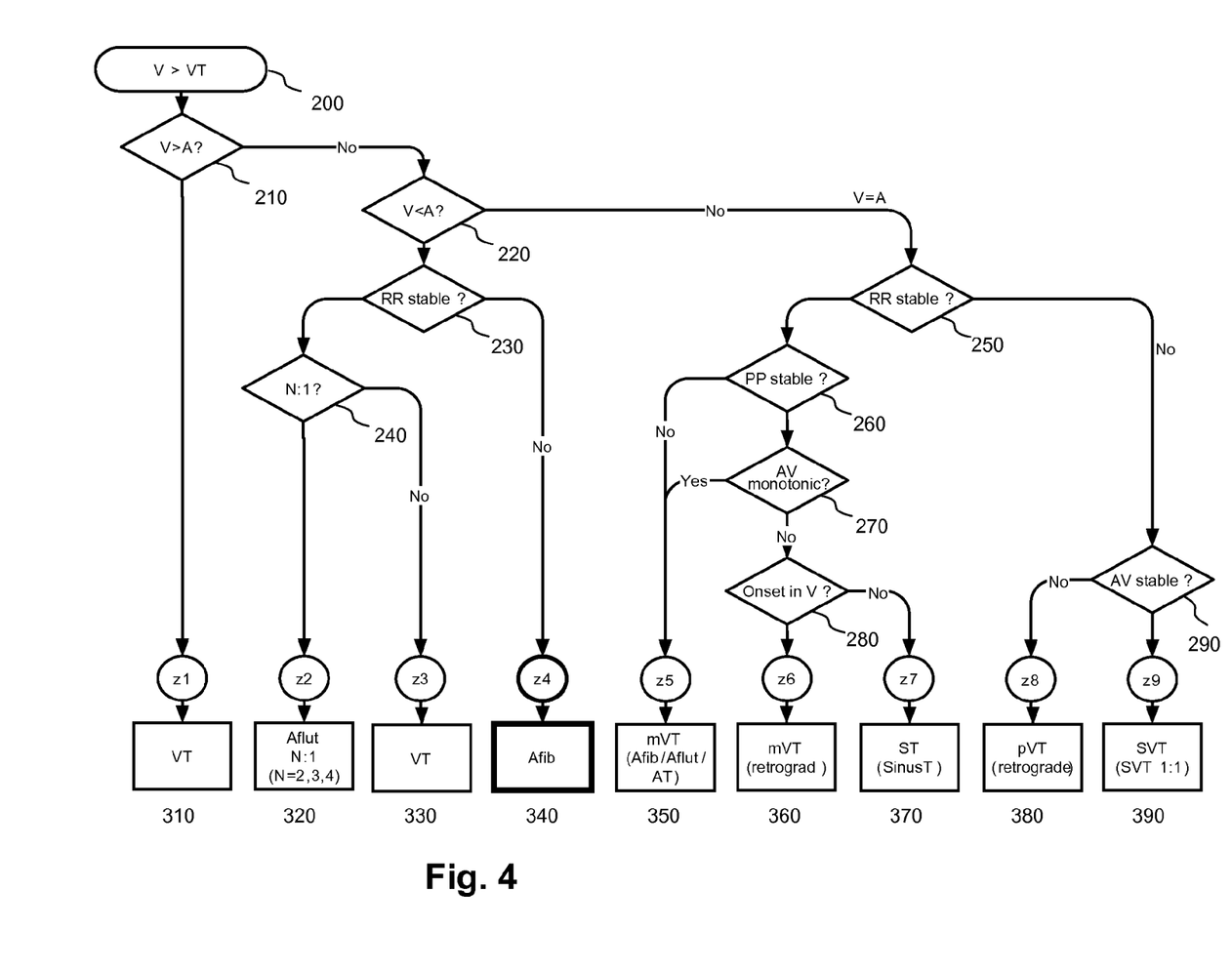
FIG. 4 shows a diagram to illustrate the function of the discrimination unit in classification of tachycardiac arrhythmias.

FIG. 4 shows a decision tree of the VT/SVT classifier of the VT/SVT discrimination unit 170 in detail.

Whenever a ventricular event (V) is detected (200) as being faster than a programmed tachycardia frequency, then first a check is performed on whether the current ventricular event is faster than the current atrial event (A) (210). If V is faster than A, then the classification as a ventricular tachycardia is made (310; VT) and the corresponding detection counter (z1) is incremented.

If V is slower than A (220), then a check is performed on whether the RR intervals are stable (23). If the RR intervals are stable, a check for a fixed N:1 conduction behavior (240) is performed. If this is the case, then an atrial flutter (310: AFlut) is classified and the SVT counter z2 is incremented.

If no fixed conduction is detectable, then a ventricular tachycardia VT (330) is classified and z3 is incremented.

If the RR intervals are evaluated as unstable (230), then an atrial fibrillation (AFib) is classified as the cause of the rapid ventricular frequency and the detection counter z4 is incremented (340). This detection counter is used for the cardioversion decision. If the atrial and ventricular frequencies are identical (V=A), a check is performed to determine whether the RR intervals are stable (250). If the RR intervals are stable, then PP stability (260) and AV monotony (270) are checked. If PP intervals are unstable or there is AV monotony, then the ventricular tachycardia is classified as a monomorphic VT with simultaneous atrial tachyarrhythmia (350: mVT with AFib, AFlut or AT) and the detection counter z5 is incremented. If PP intervals are stable, however, and there is no AV monotony, then the tachycardia is classified as retrograde VT conduction (mVT retrograde) when the ventricular onset criterion (180) is met. The detection counter z6 is then incremented.

If the onset criterion (280) is not met, a sinus tachycardia (370: SinT) is classified and the detection counter z7 is incremented. If an unstable ventricular rhythm is detected in the RR stability check (250), then the check of AV interval stability (290) decides about classification as retrograde polymorphic VT conduction (280: pVT) in the case of unstable AV intervals. The detection counter z8 is then incremented. However, if AV intervals are stable, an SVT with antegrade 1:1 conduction is classified (390: SVT 1:1) and the detection counter z9 is incremented.

The VT/SVT discrimination unit 170 illustrated in FIG. 3 decides about the delivery of treatment on the basis of the detection counter readings (310-390) depicted in FIG. 4, and it triggers the treatment control unit 190 accordingly.

For the automatic atrial cardioversion described in the present invention, the detection counter z4 illustrated in FIG. 4 is analyzed. If the counter reading exceeds a predefined value, then the classified tachyarrhythmia is considered as an atrial fibrillation with tachycardiac conduction into the ventricle. If in this case the automatic cardioversion parameter is activated, then at least one cardioversion shock is requested by the detection unit. The shock delivery control and synchronization correspond to a ventricular defibrillation shock, but with the requirement that the delivery of the shock must be synchronized with an R wave.

Figure 5:
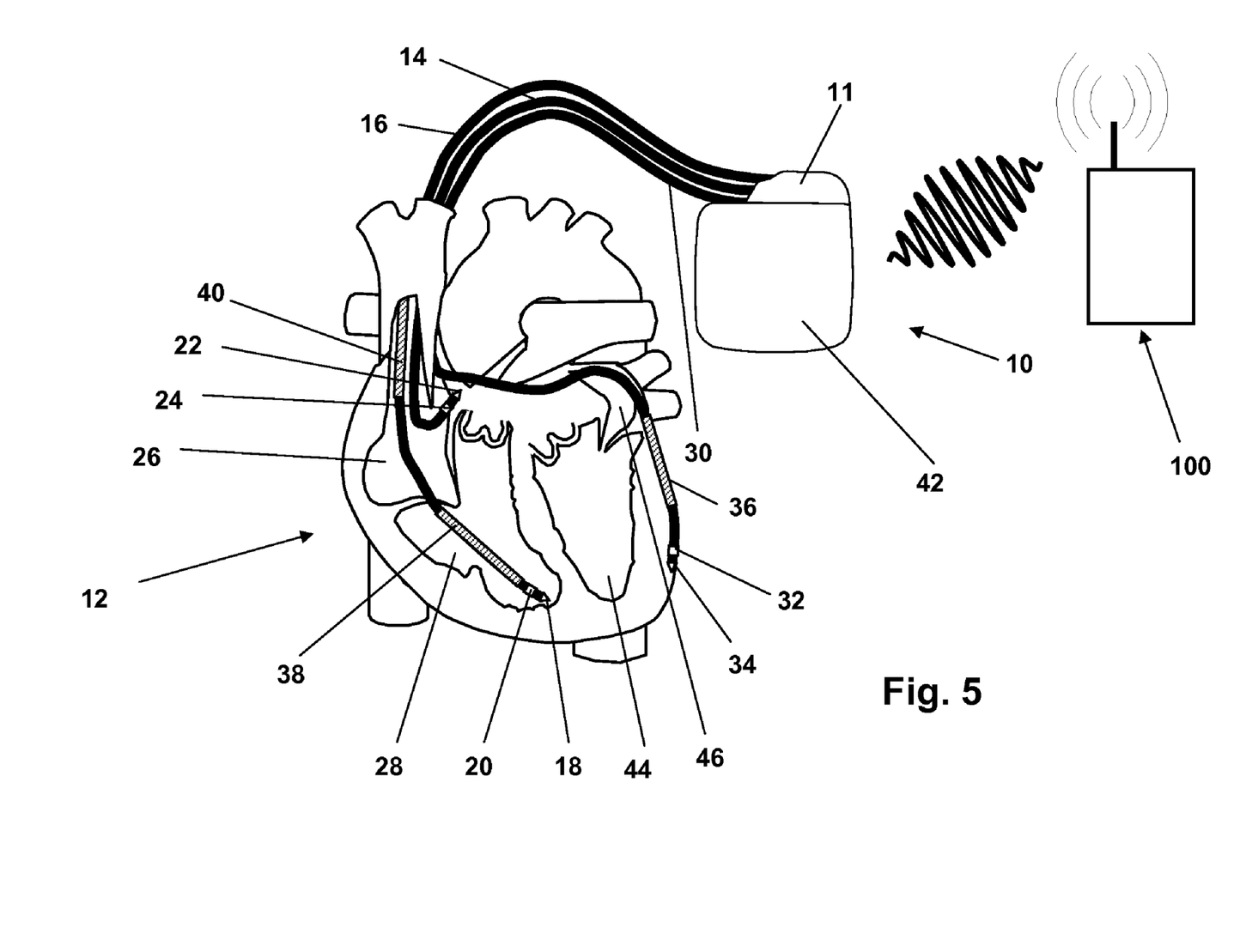
FIG. 5 shows an alternative embodiment of a cardiac stimulator in the form of a biventricular three-chamber cardiac pacemaker.

FIG. 5 shows an alternative embodiment variant of an implantable cardiac stimulator in the form of a biventricular three-chamber cardiac stimulator/ICD 10', which is connected by a terminal block 11 (header) to a right-ventricular electrode line 16, a right-atrial electrode line 14 and also a left-ventricular electrode line 30.

These electrode lines are permanently implanted in the heart 12. The right-ventricular electrode line 16 has a bipolar stimulation and detection electrode with a tip electrode 18 and ring electrode 20. Furthermore, this electrode line is equipped with a distal shock coil 38 and also with a proximal shock coil 40. The distal shock coil 38 is arranged so that it is situated in the right ventricle 28. The proximal shock coil 40 is in the upper part of the right atrium 26. The atrial electrode line 14 has a bipolar stimulation and detection electrode on the distal end consisting of the tip electrode 22 and the ring electrode 24 implanted in the right atrium 26. The left-ventricular electrode line 30 has a bipolar stimulation and detection electrode on the distal end with a tip electrode 34 and a ring electrode 32. Furthermore, this electrode line is equipped with a shock coil 36.

This shock coil 36 is arranged so that it extends from the left ventricle 44 up to the left atrium 46. The electrically active housing 42 of the implant 10 forms another electrode for delivery of the shock.

The left-ventricular electrode line 30 passes from the right atrium 26 of the heart 12 through the coronary sinus into a lateral vein branching off from the latter and is therefore also known as a coronary sinus electrode line or CS electrode line.

As can be deduced from FIG. 2 on the basis of the components shown with dotted lines, the terminal for the left-ventricular tip electrode (LV tip) and the terminal for the left-ventricular ring electrode (LV ring) are each connected to a left-ventricular stimulation unit 64 and a left-ventricular sensing unit 66. The left-ventricular stimulation unit 64 and the left-ventricular sensing unit 66 are likewise connected to the stimulation control unit 54. Both function like the stimulation units 56 and 60 and the sensing units 58 and 62 already described.

The left-ventricular shock coil 36 is also connected to the shock generator 50 by a terminal LV coil and an electrode selector unit 52. By means of the electrode selector unit 52, the control 54 may select two or more electrodes (including the conductive housing 42) by which a shock is to be delivered.

The cardiac stimulator 10' illustrated in FIG. 5 therefore offers the possibility of adjusting the shock paths for atrial cardioversion and ventricular defibrillation separately as a function of the primary cause of the ventricular tachycardia.

Figure 6:
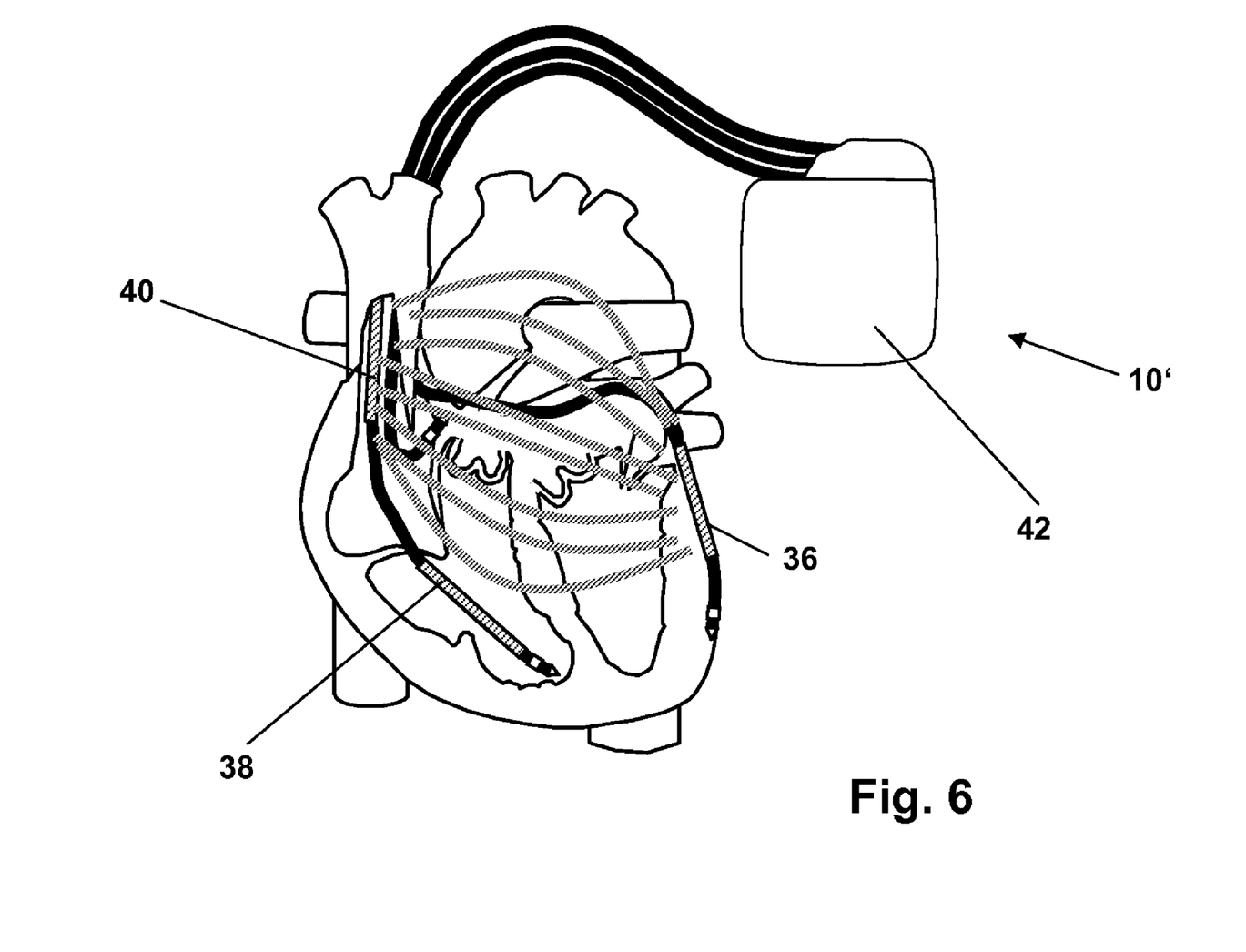
FIG. 6 shows an illustration of a shock path for ventricular defibrillation.

FIG. 6 shows the shock path for atrial cardioversion. The shock energy here is delivered between the right-ventricular proximal shock coil 40 and the left shock coil 36. In cardioversion, the largest possible atrial muscle mass, in particular including the left atrium, is covered by the electric field. Atrial cardioversion is always synchronized with ventricular stimulation to thereby minimize the risk of a ventricular acceleration.

Figure 7:
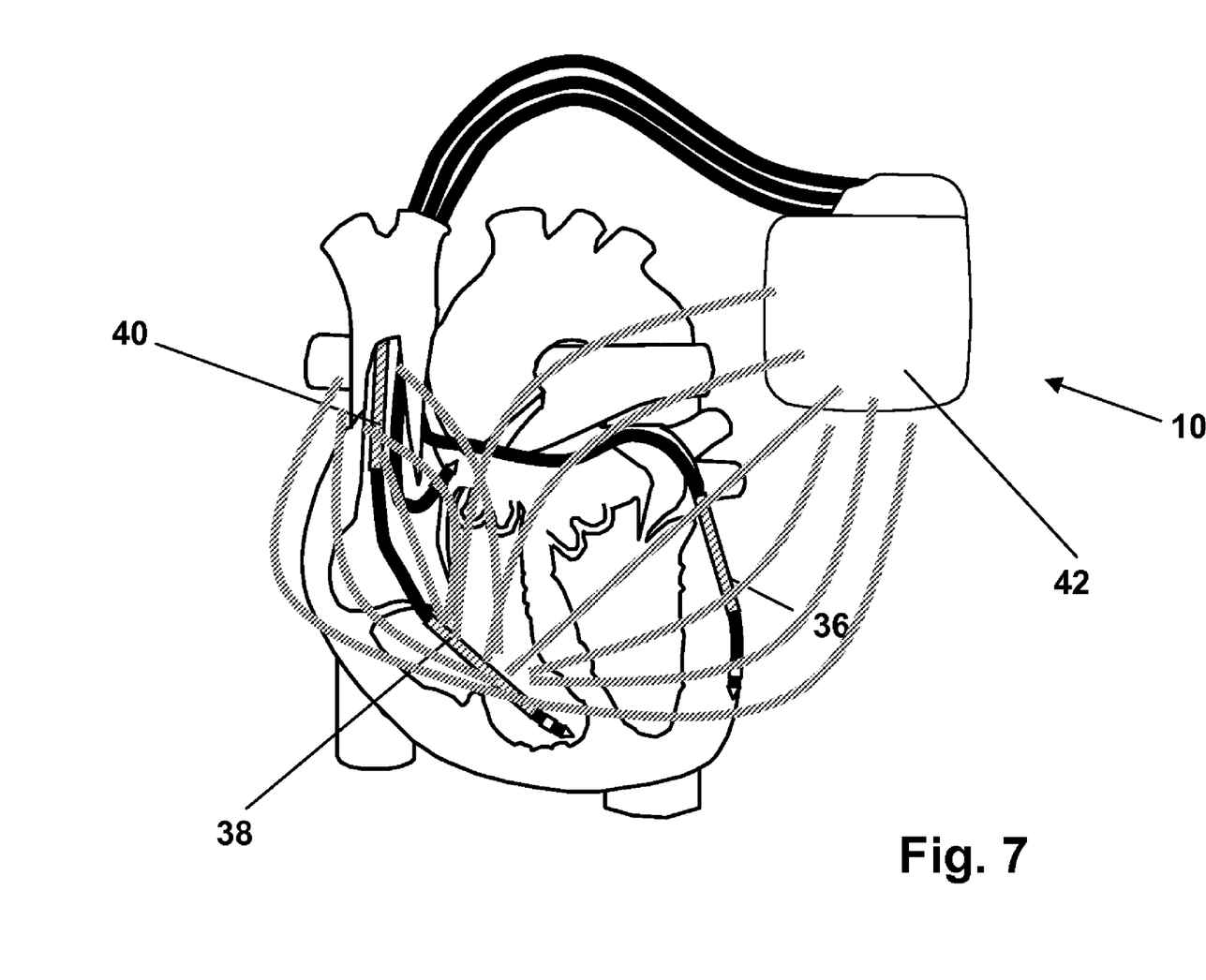
FIG. 7 shows an illustration of a shock path for an atrial cardioversion.

FIG. 7 shows the flow path configuration for ventricular defibrillation, triggered by the detection counter z3 (330) from FIG. 4, for example. In this case, the shock energy is delivered between the distal right-ventricular shock coil 38, the proximal shock coil 40 and the active housing 42 of the implant, whereby the housing 42 and the proximal shock coil 40 are switched to the same potential at the moment of shock delivery. The largest possible ventricular muscle mass is therefore included in defibrillation. This shock path configuration corresponds to the standard setting on most ventricular ICDs.

To minimize the risk of a stroke triggered by a thrombus released in atrial cardioversion, the physician can prevent a cardioversion shock from being delivered with a programmable parameter in patients lacking adequate antithrombotic medication if there has been uninterrupted atrial fibrillation prior to the cardioversion attempt. This function is already known.

What is claimed is:

1. An implantable cardiac stimulator including:
   a. a cardioversion/defibrillation unit:
      (1) in communication with at least one electrode pair, and
      (2) being adapted to deliver cardioversion shocks through the electrode pair;
   b. an atrial sensing unit:
      (1) identifying an atrial contraction, and
      (2) outputting an atrial sensing signal when an atrial contraction is identified;
   c. a ventricular sensing unit:
      (1) identifying a ventricular contraction, and
      (2) outputting a ventricular sensing signal when a ventricular contraction is identified;
   d. a tachycardia detection unit:
      (1) receiving the atrial and ventricular sensing signals from the atrial sensing unit and ventricular sensing unit,
      (2) identifying a tachycardia therefrom, the identified tachycardia including one or more of:
         (a) a ventricular tachycardia (VT) or
         (b) a supraventricular tachycardia (SVT);
      wherein the tachycardia detection unit further identifies any atrial fibrillation (AFib) giving rise to a supraventricular tachycardia (SVT);
   e. a treatment control unit triggering an atrial cardioversion shock by the cardioversion/defibrillation unit when:
      (1) the rhythm of the ventricular contractions identified by the ventricular sensing unit is greater than a predefined frequency limit, and
      (2) the tachycardia detection unit identifies a supraventricular tachycardia (SVT) arising from an atrial fibrillation (AFib).

2. The implantable cardiac stimulator of claim 1 wherein the control unit triggers an atrial cardioversion shock when the rhythm of the ventricular contractions detected by the ventricular sensing unit is also less than the frequency of the atrial contractions detected by the atrial sensing unit.

3. The implantable cardiac stimulator of claim 2 wherein the control unit triggers an atrial cardioversion shock when the rhythm of the ventricular contractions detected by the ventricular sensing unit is also irregular.

4. The implantable cardiac stimulator of claim 1 wherein the control unit synchronizes the triggering of an atrial cardioversion shock with a ventricular contraction detected by the ventricular sensing unit.

5. The implantable cardiac stimulator of claim 1 wherein the cardioversion/defibrillation unit is in communication with at least three shock electrodes through which cardioversion shocks can be delivered, the shock electrodes including:
   a. a distal shock coil,
   b. a proximal shock coil, and
   c. an electrically conductive housing of the implantable cardiac stimulator.

6. The implantable cardiac stimulator of claim 1 wherein:
   a. the cardioversion/defibrillation unit is in communication with:
      (1) an atrial cardioversion shock electrode, and
      (2) a ventricular defibrillation shock electrode spaced from the atrial cardioversion shock electrode,
   b. the treatment control unit can trigger both:
      (1) atrial cardioversion shocks via the atrial cardioversion shock electrode, and
      (2) ventricular defibrillation shocks via the ventricular defibrillation shock electrode,
   wherein the atrial cardioversion shocks and ventricular defibrillation shocks travel along different shock paths.

7. The implantable cardiac stimulator of claim 1:
   a. wherein the cardioversion/defibrillation unit is in communication with:
      (1) a right-atrial electrode line,
      (2) a right-ventricular electrode line, and
      (3) a left-ventricular electrode line,
   b. further including a left-ventricular sensing unit in communication with a sensing electrode on the left-ventricular electrode line, the left-ventricular sensing unit identifying a left-ventricular contraction.

8. The implantable cardiac stimulator of claim 7 wherein the control unit synchronizes any triggered atrial cardioversion shock with a left-ventricular contraction detected by the left-ventricular sensing unit.

9. The implantable cardiac stimulator of claim 1 wherein:
   a. any atrial fibrillation (AFib) is monitored to determine whether it exceeds a predefined period of time without interruption, and
   b. the treatment control unit triggers the atrial cardioversion shock only if the predefined period of time has been exceeded.

10. The implantable cardiac stimulator of claim 1 further including:
    a. a telemetry unit configured to provide bidirectional wireless data transmission, and
    b. a memory configured to store transmitted data,
    wherein at least the predefined frequency limit is wirelessly transmitted to the implantable cardiac stimulator via the telemetry unit and stored in the memory.

11. An implantable cardiac stimulator including:
 a. first and second shock coils, the shock coils being spaced apart and supplied by separate leads,
 b. a tachycardia detection unit:
  (1) receiving signals indicating the timing of atrial contractions and ventricular contractions of a heart,
  (2) identifying a tachycardia from the atrial contractions and ventricular contractions where the rhythm of the ventricular contractions is greater than a predefined frequency limit, the identified tachycardia including:
   (a) a ventricular tachycardia (VT) where the rhythm of the ventricular contractions is also greater than the rhythm of the atrial contractions;
   (b) an atrial fibrillation (AFib) where the rhythm of the ventricular contractions is also:
    (i) less than the rhythm of the atrial contractions, and
    (ii) irregular,
 wherein:
  I. an atrial cardioversion shock is delivered via the first shock coil when an atrial fibrillation (AFib) is identified, and
  II. a ventricular defibrillation shock is delivered via the second shock coil when a ventricular tachycardia (VT) is identified.

12. The implantable cardiac stimulator of claim 11 wherein the delivery of the atrial cardioversion shock is timed in dependence on the ventricular contractions.

13. The implantable cardiac stimulator of claim 11 wherein the delivery of the atrial cardioversion shock only occurs if the atrial fibrillation (AFib) conditions are present for longer than a predefined period of time.

14. The implantable cardiac stimulator of claim 11 wherein the first and second shock coils are situated on a common ventricular electrode line.

15. The implantable cardiac stimulator of claim 11 wherein:
 a. the first shock coil is a proximal shock coil situated on an electrode line, and
 b. the second shock coil is a distal shock coil situated on the electrode line, the distal shock coil being situated closer to an end of the electrode line than the proximal shock coil.

16. The implantable cardiac stimulator of claim 11 wherein:
 a. the first shock coil is situated in or adjacent one of the ventricles of the heart, and the atrial cardioversion shock is delivered between the first shock coil and a ventricular shock coil situated in or adjacent the other of the ventricles of the heart;
 b. the second shock coil is situated in the same ventricle of the heart as the first shock coil, and the ventricular defibrillation shock is delivered between the first and second shock coils.

17. The implantable cardiac stimulator of claim 16 wherein the ventricular defibrillation shock is also delivered between:
 a. at least one of the first and second shock coils, and
 b. a housing of the implantable cardiac stimulator.

18. An implantable cardiac stimulator including:
 a. an atrial cardioversion shock electrode in communication with a heart,
 b. a tachycardia detection unit:
  (1) receiving signals indicating the timing of atrial contractions and ventricular contractions of the heart,
  (2) triggers an atrial cardioversion shock via the atrial cardioversion shock electrode where atrial fibrillation (AFib) conditions are present, the atrial fibrillation (AFib) conditions being characterized by:
   (a) the rhythm of the ventricular contractions is greater than a predefined frequency limit,
   (b) the rhythm of the ventricular contractions is less than the rhythm of the atrial contractions, and
   (c) the rhythm of the ventricular contractions is irregular.

19. The implantable cardiac stimulator of claim 18 wherein the atrial cardioversion shock is synchronized with the ventricular contractions.

20. The implantable cardiac stimulator of claim 18 wherein triggering of the atrial cardioversion shock only occurs if the atrial fibrillation (AFib) conditions are present for longer than a predefined period of time.

* * * * *